United States Patent [19]

Maeno et al.

[11] Patent Number: 4,890,054
[45] Date of Patent: Dec. 26, 1989

[54] APPARATUS AND METHOD FOR MEASURING PHYSICAL QUANTITIES

[75] Inventors: Yorihiko Maeno; Shigeyasu Higashi, both of Tokyo, Japan

[73] Assignee: Dipole Electronics Co., Ltd., Tokyo, Japan

[21] Appl. No.: 243,336
[22] PCT Filed: Dec. 8, 1987
[86] PCT No.: PCT/JP87/00950
   § 371 Date: Jul. 15, 1988
   § 102(e) Date: Jul. 15, 1988
[87] PCT Pub. No.: WO88/04423
   PCT Pub. Date: Jun. 16, 1988

[30] Foreign Application Priority Data

Dec. 9, 1986 [JP] Japan ................... 61-293026

[51] Int. Cl.⁴ ............................................. G01N 22/00
[52] U.S. Cl. ........................ 324/58.5 A; 324/58.5 C
[58] Field of Search ............. 324/58 A, 58 C, 58.5 A, 324/58.5 C

[56] References Cited

U.S. PATENT DOCUMENTS

| | | | |
|---|---|---|---|
| 3,079,551 | 2/1963 | Walker | 324/58 A |
| 4,581,575 | 4/1986 | Osaki et al. | 324/58.5 C |
| 4,600,879 | 7/1986 | Scullyet | 324/58.5 A |
| 4,620,146 | 10/1986 | Ishikawa et al. | 324/58.5 A |
| 4,673,895 | 6/1987 | Tadachi et al. | 333/227 |
| 4,781,063 | 11/1988 | Osaki et al. | 324/58.5 C |

FOREIGN PATENT DOCUMENTS

| | | |
|---|---|---|
| 392151 | 3/1939 | Japan . |
| 58-30534 | 6/1983 | Japan . |
| 61-62845 | 3/1986 | Japan . |
| 62-124449 | 6/1987 | Japan . |
| 62-169041 | 7/1987 | Japan . |
| 398896 | 2/1974 | U.S.S.R. ................... 324/58.5 C |

Primary Examiner—Gerard R. Strecker
Assistant Examiner—Maura K. Regan
Attorney, Agent, or Firm—Frishauf, Holtz, Goodman & Woodward

[57] ABSTRACT

An apparatus for measuring physical quantities comprises a microwave cavity resonator (1) provided with a protrusion (4) on its axis. An object (2) to be measured is placed in the central portion (17) of the protrusion (4) in parallel with it, or the object (2) to be measured is placed vertically against the protrusion (4), so that an electric field can be confined to the area to be measured. This results in precise measurement of physical quantities on a minute portion of the object to be measured. A method of measuring physical quantities comprises obtaining moisture content x (g/m²) and basis weight y (g/m²) of the object to be measured from equations having at least a product term of moisture content x and basis weight y, and by measuring the frequency and the voltage of microwave energy at the maximum resonance point on the object to be measured. This enables obtaining easily and accurately the moisture content and basis weight of the object to be measured.

20 Claims, 6 Drawing Sheets

FIG. 6
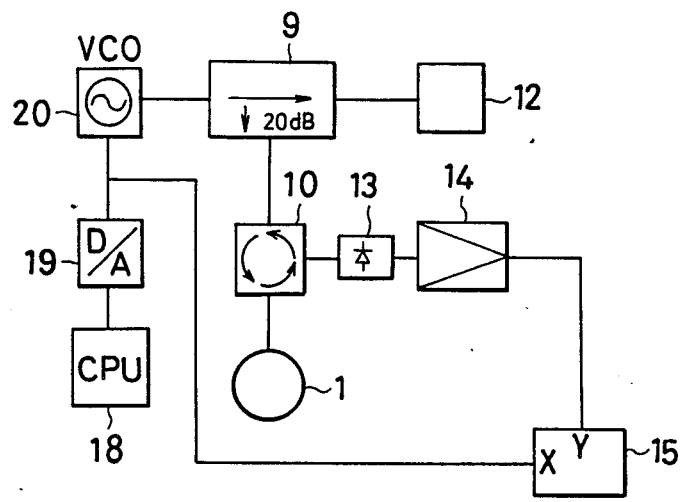
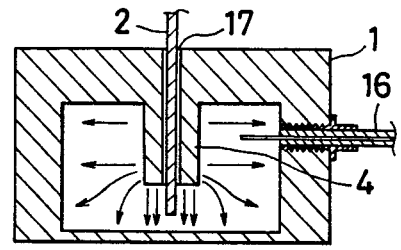
FIG. 10
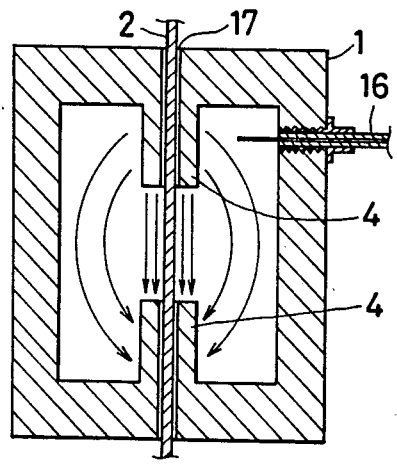
FIG. 11

APPARATUS AND METHOD FOR MEASURING PHYSICAL QUANTITIES

FIELD OF THE INVENTION

The present invention relates to an apparatus and a method for measuring physical or chemical properties of materials by absorption quantities of microwave energy or a shift in resonant frequency of a cavity.

DESCRIPTION OF THE PRIOR ART

The technology of measuring moisture content of paper and others, by means of microwave energy in an on-line manner in the paper-production process, has been noticed recently. It is desirable that the moisture content can be always measured and fed back, in an on-line manner, to the process of adjusting or drying raw material of pulp in order to maintain a good quality of finished paper. In addition, a paper price is determined by a paper weight per unit area on taking delivery from a factory. It is also attempted to make the paper have a moisture content as high as possible without deteriorating its quality. Therefore, measuring the moisture content accurately on-line is very important in not only paper-production processes but also in many other technical fields. As shown in Japanese Patent Publication No. 58-30354, the prior method of measuring moisture content of the object is to measure a difference in microwave energy and a shift in a resonant frequency between cases when a sheet object is inserted, and when not inserted, in a gap formed between an upper rectangular prism provided with means for emitting microwave energy and a lower rectangular prism provided with means for receiving microwave energy.

Each of the upper and lower typical rectangular prisms of cavity resonators in the prior method has an opening cross-section of about 30 cm×60 cm, and a depth of about 70 cm. An intermediate gap formed between an upper and a lower prism is about 1 cm. Since 3 GHz is primarily used for microwave oscillators including circuits which are commercially available, these dimensions of the cavity and this gap width have been adopted in order to suit the frequency.

There are four problems in measuring moisture content by means of the conventional rectangular prism cavity resonator when manufacturing paper.

The first problem is that the opening of the resonator cannot be smaller than 30 cm×60 cm. It is necessary to measure moisture content in an area as small as possible in practice. In the production of paper, especially, it is most important to adjust the moisture content contained in the width of about 10 cm from the edge of the paper to an adequate value. However it has been very difficult to make such measurement by using the conventional technique.

The second problem is that because the conventional cavity shaped like a rectangular prism has a low Q-value, the Q-value and resonant frequency of microwave energy do not vary sensitively when the object is inserted or even when its moisture content varies. Therefore the accuracy of measurement has been extremely poor.

The third problem is that if the upper and lower cavity resonators with the same dimensions are displaced relative to each other along the plane of a sheet object in the case of on-line measurement, the required measurement, then, cannot be conducted. This is because in that case, the cavity resonator does not function properly even if the dislocation is small. Therefore, this greatly reduces the stability of on-line measurement in the production of objects such as paper.

The fourth problem is the difficulty of realizing an accurate rectangular prism shape in practice because the demand of accuracy for dimensions of the cavity resonator is very severe. In case of constructing an accurate rectangular prism cavity by pasting plate members together, it is difficult to maintain parallelism at the position where the members are placed together. As a result, in practice, preventing microwave energy loss induced by the psuedomorphic cavity becomes difficult. In other words, it is difficult to make the cavity of a precise configuration having a Q-value similar to a theoretical value.

A typical prior method for the measurement of moisture content is based upon empirical determination of proportional constants on the assumption that the maximum resonant voltage V of microwave energy is proportional only to moisture content in the paper inserted in the gap formed between two cavities. Even slight changes in measurement environment, such as temperature or moisture, extremely affect the measuring results of moisture content. Thus, this kind of conventional method needs calibration curves for each apparatus, which calibration curves are difficult to handle, very complicated, and dependent on skill and experience. As a result, the measurement accuracy varies from several % to over 5% in the effective measurement of 3–13% when measuring moisture content, so that one will find little reliability, reproductivity and stability in measurement.

On the other hand, a microwave cavity resonator has never been used for the measuring of paper weight (mass per unit area). $\beta$ rays, being dangerous to use, have been adopted to measure said paper weight in the paper production processes. The accuracy of the paper weight measurement using $\beta$ radiation varies by 3 g/m$^2$ in an effective measurement range of 10 g/m$^2$–800 g/m$^2$, which leads to unsatisfactory accuracy.

SUMMARY OF THE INVENTION

The object of the present invention is to provide a microwave re-entrant cavity resonator which enables the accurate measurement of physical quantities in a minute portion of sheet materials.

Another object of the present invention is to provide a microwave re-entrant cavity resonator which enables the precise measurement of physical quantities of stringy materials.

Still another object of the present invention is to provide a method for precise measurement of moisture content and weight of an object by means of a microwave cavity resonator.

According to the invention, there is provided a microwave cavity resonator having a pair of electrodes, the upper electrode being provided with means for emitting microwave signals and the lower electrode being provided with means for receiving microwave signals, characterized in that a protruding portion is provided on the part corresponding to at least one of the electrodes. According to this configuration, the distribution of electric field density of microwave energy which is irradiated to the object, can be greatly increased at the vicinity of the protruding portion. As a result, the area to be measured can be confined to the same area as the protruding portion, and at the same time, changes in Q-value and resonant frequency obtained from a cavity resonator can be made sensitive.

According to the invention, there is provided another apparatus for measuring physical quantities comprising a cylindrical microwave cavity resonator equipped with microwave energy emitting means and microwave energy receiving means, characterized in that a hole is provided in the center of said protruding portion for holding the object. By means of this configuration, stringy materials can be placed at the region where the electric field is the largest, so that the physical quantities can be measured precisely.

the invention provides a method of measuring moisture content x and weight y of the sheet material by using a microwave cavity resonator, characterized in that after every proportional constant in the following characteristic equation having at least a product term xy $$f = F_0 + F_1 \cdot x + F_2 \cdot y + F_3 \cdot xy + \ldots$$

$$v = V_0 + V_1 \cdot x + V_2 \cdot y + V_3 \cdot xy + \ldots$$

is determined by measuring frequency f and voltage v on the maximum resonant point of microwave energy on the sample of which moisture content $x(g/m^2)$ and weight $y(g/m^2)$ are previously known, moisture content x and weight y of the material to be measured are calculated from the characteristic equation using measured frequency f and voltage v of the material.

This measuring method achieves a great improvement in measurement accuracy of moisture content and weight.

BRIEF DESCRIPTION OF THE DRAWINGS

FIG. 6 shows a circuit diagram used for the apparatus of the invention;

FIGS. 10 and 11 show modified examples of the apparatus of the second embodiments of the present invention.

DETAILED DESCRIPTION

Figure 1A:
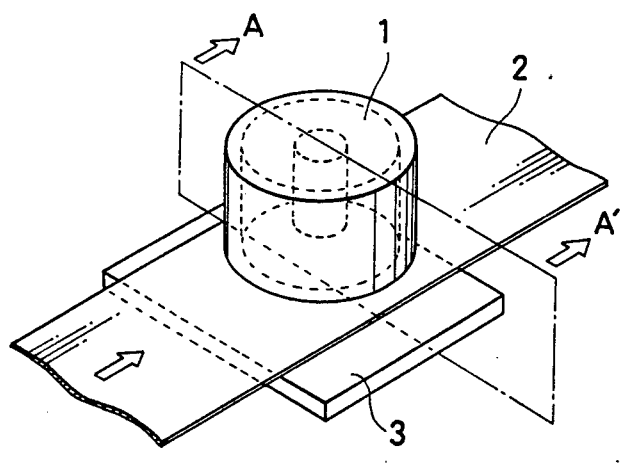
FIG. 1A is an apparatus for measuring physical quantities according to the invention.

FIG. 1A shows a typical apparatus of the present invention for measuring physical quantities of sheet material. A cylindrical re-entrant cavity resonator 1 which is axially symmetrical, is provided with microwave energy emitting means and microwave energy receiving means not shown in the figure. This Figure shows the moisture content of paper in the paper production process being measured in an on-line manner. Object 2 to be measured can be any kind of sheet materials such as grains, various materials of fluid particulate e.g. for forming ceramic, stringy materials, corrugated fiberboard material, various laminates coated like a film base, etc. Even if the object 2 is particulate or fluid, it can be measured as long as it can be converted into a sheet-like shape. Since the object 2 to be measured is inserted into the gap between lower portion of resonator 3 and cavity resonator 1 without contact, measurement can be conducted in a non-contact and on-line manner.

Figures 1B, 1C:
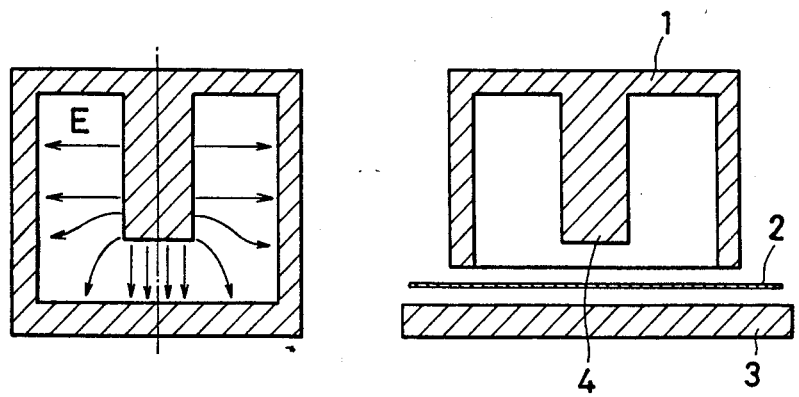
FIG. 1B is a sectional view taken on line A—A' of FIG. 1A.
FIG. 1C is a drawing to show the principle of the apparatus of the invention.

FIG. 1B shows a longitudinal sectional view taken on lines A—A' of FIG. 1A for explaining the structure of the apparatus in FIG. 1A. FIG. 1B shows that protrusion 4 faces the paper 2 which is the object. As shown in FIG. 1C, strong electric fields emitted from the vicinity of the top portion of protrusion 4 distribute vertically against the object. Thus, the portion to be measured is confined to the area which is almost the same as one of the top portion of the protrusion, so that the moisture content of the minute area of the object can be measured. The cavity resonator of an embodiment made of aluminum, whose outer and inner radii are 2.54 cm and 0.9 cm respectively, has a cavity length of 2.99 cm. When the separation between the top of the protrusion 4 and lower part 3 of the cavity is 1.35 cm, a resonance frequency of 2.9 GHz and a Q-value of 7097 are obtained experimentally. It is found that those values are in good agreement with the calculated ones. It should be noted that the full band width at half maximum is only 380 kHz at the resonant frequency of 2.9 GHz, which is extremely narrow. This means that a high Q-value can be obtained by the apparatus of the present invention. In the conventional rectangular prism cavity resonator having a resonant frequency of 2.9 GHz, the Q-value is about 5500 and the half band width is as broad as 700 kHz. Thus, the resonator of the present invention has a greater sensitivity than the conventional one.

Another advantage of the apparatus of the invention is that the configuration formed by two electrodes of the cavity resonator does not change even if the concave cylindrical cavity resonator 1 moves horizontally at the time of measuring, because the lower part 3 of the resonator is flat. Therefore, stable measurement can be attained.

In addition, the apparatus is easy to manufacture because it is axially symmetrical and cylindrical.

Figure 2A:
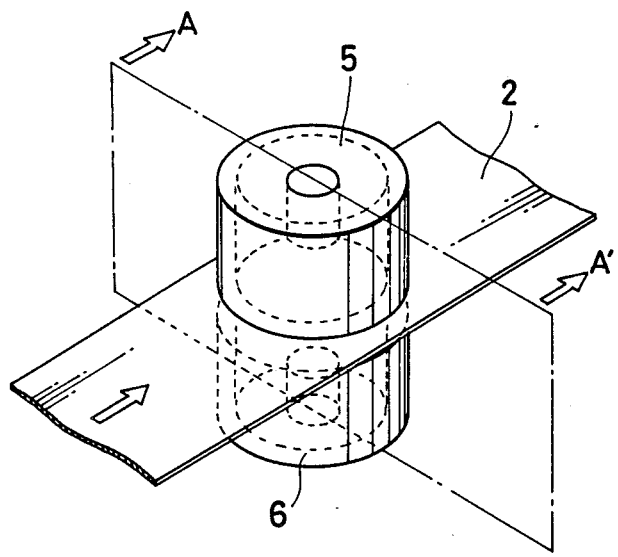
FIG. 2A is a perspective view of a modified example of the apparatus of FIG. 1A.
Figures 2B, 2C:
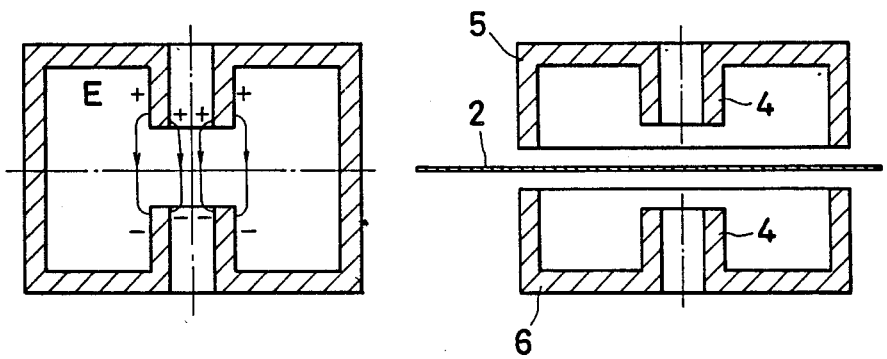
FIG. 2B is a sectional view taken on line A—A' of FIG. 2A.
FIG. 2C is a drawing to show the principle of the apparatus of FIG. 1A.

FIG. 2A is a modified example of the apparatus shown in FIG. 1A for measuring physical quantities. FIG. 2B is a cross-sectional view taken on line A—A' of FIG. 2B and FIG. 2C shows the measurement principle of the apparatus. In FIGS. 2A and 2B, upper cylindrical cavity resonator 5 and lower cylindrical cavity resonator 6 face each other, and the object 2 to be measured, such as paper, is inserted between them. Upper and lower cylinders have respectively a protrusion 4 provided with a penetrating hole, as shown in cross-section in FIG. 2B, the holes in the protrusion being precisely lined up between both resonators. FIG. 2C shows that the distribution of the electric field is dense in the vicinity of the top portion of said protrusion and is vertical against the object. Upper and lower cylindrical cavity resonators do not necessarily have the same shape. It is only necessary that their shape gives rise to the electric field distribution at the vicinity of the top portion in the protrusion as shown in FIG. 2C.

Figure 3A:
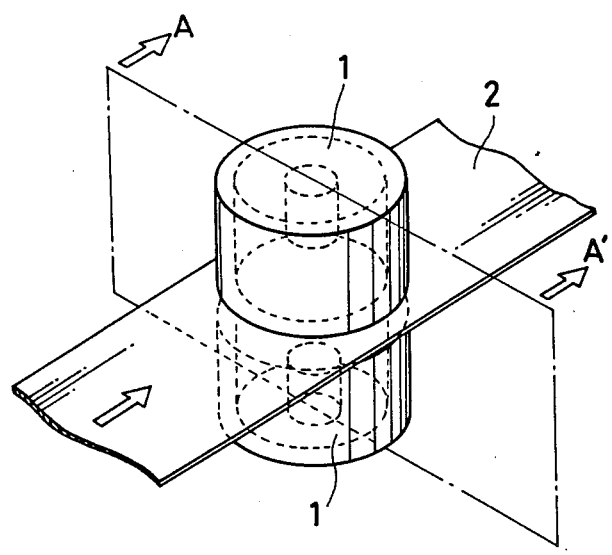
FIG. 3A is a perspective view of another example of the apparatus of FIG. 1A.
Figure 3C:
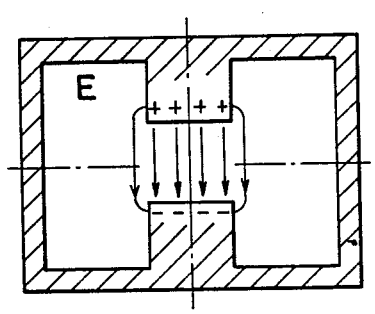
FIG. 3C is a drawing to show the principle of the apparatus of FIG. 3A.
Figure 3B:
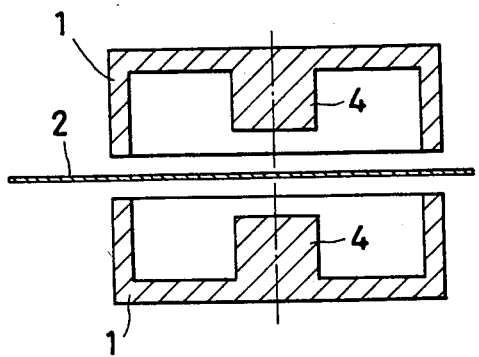
FIG. 3B is a sectional view taken on line A—A' of FIG. 3A.

FIG. 3A is another modified example of the apparatus of FIG. 1A for measuring physical quantities. FIG. 3B is a cross-sectional view taken on line A—A' of FIG. 3A, and FIG. 3C is a drawing to show the principle thereof. This apparatus corresponds to the one in which the hole in the apparatus of FIG. 2A is filled up. This system comprises two of the same re-entrant cavities shown in FIG. 1C. FIG. 3C shows that the electric field in the cavity resonator is extremely strong in the vicinity of the protrusion and is vertical against the object. Upper and lower re-entrant resonators do not necessarily have the same shape as in the cases mentioned above.

As described above, any kind of cavity resonator where a protrusion is provided at the area corresponding to the part to be measured, so that the electric field distribution becomes dense in the object, can be acceptable as the apparatus of the present invention for measuring physical quantities of sheet-like material.

The cavity resonator of the present invention is not limited to one made of metal, such as aluminum. It can be a cavity resonator whose body is made of plastics, and whose inside surface is coated with conductive material, such as Al or Ag, so as to decrease the weight of the resonator.

Figure 4:
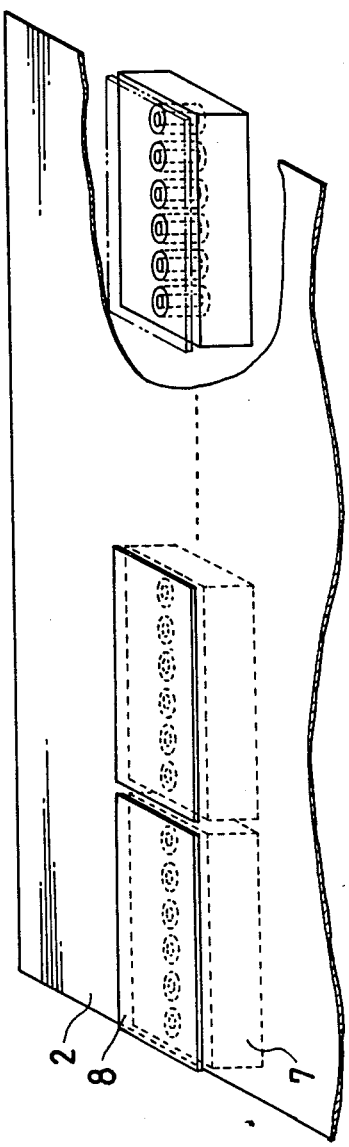
FIG. 4 shows a second embodiment of the present invention.

In the system of the present invention for measuring physical quantities shown in FIG. 4, many cavity blocks are placed in line over the whole region of the object, wherein each cavity block, of about 1 m in length, has six re-entrant type cavity resonators. Each cavity resonator in the cavity block, made of Al, has a cylindrical protrusion. Upper plate 8 facing cavity part 7 is a plate of 1 m in length which is common to six microwave cavity resonators. With this configuration where many cavity blocks are placed, one can measure the physical quantities of the whole object without the necessity of moving a cavity resonator over the whole region of the object such as in a case in which only one cavity resonator is provided for the whole region.

In the system for measuring physical quantities shown in FIG. 4, the microwave energy emitting part is not shown, but as one example, a system wherein each block of 1 m in length is provided with a microwave transmitter is acceptable. This system enables to commonly apply microwave energy to each cavity resonator in a block for microwave measurement so that only one microwave transmitter is enough for one block, which results in reduced costs of the measuring system.

Figure 5B:
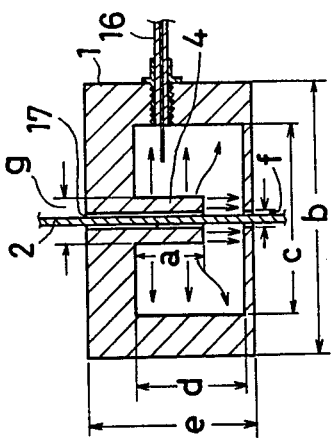
FIG. 5B is a sectional view taken on line B—B' of FIG. 5A.
Figure 5A:
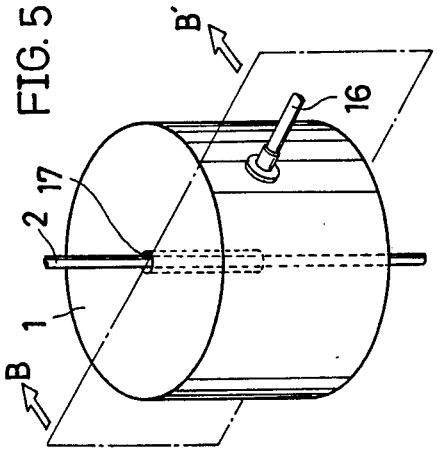
FIG. 5A is a perspective view of the apparatus of FIG. 4.

FIG. 5A is a perspective view of a cylindrical cavity resonator 1 of the present invention that is suitable for measurement of physical quantities of stringy materials. The cylindical cavity resonator 1 is made of Al, and is provided with a microwave energy emitting and receiving means 16. Reflected microwaves are received by the microwave emitting and receiving means 16. The object 2 to be measured has a shape like a pipe, rod or fiber. In the embodiment shown in FIG. 5A, the object 2 to be measured is a 0.2 mm diameter glass fiber containing minute metal pieces. The physical quantities of the object 2 are obtained from the comparison between the resonance characteristics of the glass fiber with metal pieces and the resonance characteristics of a glass fiber without metal pieces. As shown in a cross-sectional view of FIG. 5B taken on line B—B' of FIG. 5A, protrusion 4 is provided at the center of cylindrical cavity resonator 1, and space 17 is provided at the center of the protrusion 4 for placing the object therein, which enables measurement in a non-contact and on-line manner.

Concerning dimensions of every portion of cylindrical cavity resonator 1 shown in FIG. 5B, outside diameter b of the cavity is 60 mm; inside diameter c is 42 mm; the height e of the cavity is 38 mm; inside height d is 25 mm; the diameter g of the protrusion is 42 mm; the distance a between the upper edge of the cavity and the top of the protrusion is 16.1 mm; and the inside diameter of space 17 is 3.2 mm.

A circuit configuration used for an apparatus of the present invention for measuring physical quantities will be explained based on FIG. 6. D/A converter 19 converts a directing signal from CPU 18 into analog signals which are input into VCO (voltage controlled oscillator) 20 and the x axis input of x-y recorder 15. Microwaves generated at VCO 20 are applied to the cylindrical cavity resonator 1 via directional coupler 9 and circulator 10. Reflected waves in the resonator 1, after being separated by circulator 10, are applied to y axis input of x-y recorder 15 through detector 13 and amplifier 14 for recording the resonance characteristic of each object 2 to be measured.

The configuration of cylindrical cavity resonator 1 of the present invention for use with stringy materials is not restricted to the one shown in FIGS. 5A and 5B. Available are resonators wherein a hole is not provided on the bottom plate as shown in FIG. 10, or one wherein protrusions are provided on both ends as shown in FIG. 11.

The cavity resonator 1 of the present invention is not necessarily made of metal, such as aluminum. It can be one wholly made of plastics the inside surface of which is coated with conductive material, such as Al and Ag, in order to decrease its weight.

Due to the confinement effect of the electric field to the space of the protrusion electrode inside the cavity, as the above-mentioned localization effect, the Q-value and resonating frequency of the cavity change with great responsiveness responsive to only a slight change in physical quantities of objects to be measured. Thus, not only pipe-shape, rod-shape or stringy materials themselves, but also minute metal pieces contained in them can be measured precisely.

Figure 7:
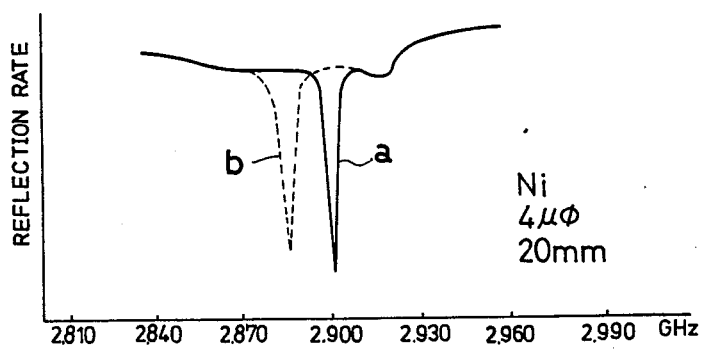
FIGS. 7-9 show measurement results obtained by the apparatus of FIGS. 5A and 5B.

FIG. 7 shows the result of the measured resonance frequency when glass fibers of 0.2 mm$\phi$, containing Ni pieces of 4 $\mu$m$\phi$ in diameter and 20 mm in length, are inserted into the space 17 of circular cavity resonator 1 as shown in FIGS. 5A and 5B. Curve "a" shows the reflection characteristics of a glass fiber of 0.2 mm$\phi$ without Ni pieces, and curve "b" shows that for such a glass fiber containing Ni pieces. According to FIG. 7, it can be seen that the resonance frequency of curve "b" is displaced by 25 MHz with reference to curve "a", because of the existence of minute Ni pieces. This concludes that the measurement apparatus for measuring physical quantities of this invention can detect minute Ni pieces with extremely great sensitivity.

Figure 8:
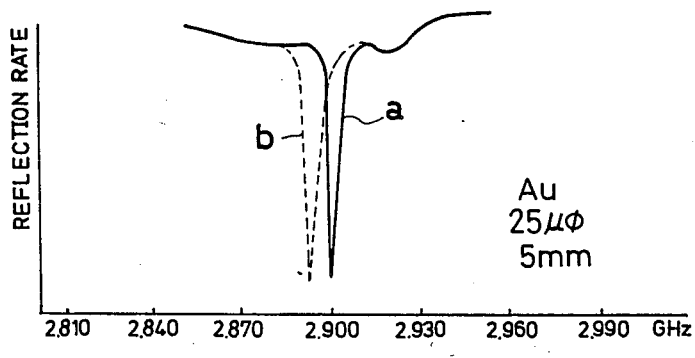

FIG. 8 shows the result of measured resonance frequency of a glass fiber of 0.2 mm$\phi$, containing Au pieces of 25 $\mu$m$\phi$ in diameter and 5 mm in length, and one of the same glass fiber without Au pieces. This example also shows that the measuring apparatus of the invention can definitely detect the existence of Au pieces.

Figure 9:
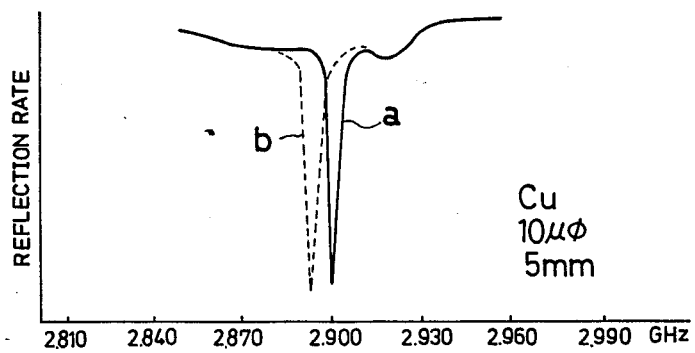

FIG. 9 shows the result of measured resonance frequency of a glass fiber of 0.2 mm$\phi$, containing Cu pieces of 10 $\mu$m$\phi$ in diameter and 5 mm in length, and one of the same glass fiber without Cu pieces.

Finally, the method of measuring of this invention using a microwave cavity resonator, which makes it easy to measure the physical quantities of the objects to be measured, will be explained.

A pair of rectangular prism cavity resonators in which two cavities with an opening of 34×76 mm and a depth of 10 mm were placed to form a gap of 10 mm, were employed for measurement using 3 GHz. The object being measured was paper. At first, the moisture content and basis weight were measured by a conventional method for 1500 samples which had been kept in a thermostatic chamber. They were obtained from 30 pieces of paper whose moisture content was in the range of 3%–13% and 50 pieces of paper whose basis weight was in the range of 10 g/m$^2$–800 g/m$^2$. Secondly, the frequency f and voltage v of maximum resonance of microwaves were measured on said 1,500 samples and 3,000 measured data items were obtained. Considering the dependency of moisture content x and basis weight y on f and v depending on those data, it was concluded that the moisture content x(g/m$^2$) and basis weight y(g/m$^2$) determined from the following equations do not differ from the true values, as long as 1st order terms and cross terms are taken into account.

$$f = F_1 \cdot x + F_2 \cdot y + F_3 \cdot xy$$

$$v = V_1 \cdot x + V_2 \cdot y + V_3 \cdot xy$$

In the case of paper measurement, it is not necessary to consider the terms of higher than second order. By using said 3,000 data items, proportional constants were determined as follows:

$F_1 = 0.341$, $F_2 = 25.479$, $F_3 = -8.575 \times 10^{-3}$ $V_1 = 2.547$, $V_2 = 29.643$, $V_3 = -0.144$ According to the above equations, the moisture content x and basis weight y of the object, such as paper, can be easily obtained by measuring only frequency f and voltage v of the maximum resonance of the microwaves.

It was already mentioned that the resonance voltage v is eminently affected by the phenomena that water absorbs microwaves, but the above equations reflect this phenomena. In addition, they apparently represent other factors which could not be predicted quantitatively beforehand.

Using the techniques of the present invention, it is assured to measure moisture content with an accuracy of 0.3 g/m$^2$ in the effective measuring range 3%–13%. Concerning basis weight, an accuracy of 0.3 g/m$^2$ was obtained in the range of 10 g/m$^2$. In both cases, measurement was scarcely affected by measurement environment.

Although the invention was explained with reference to rectangular prism cavity resonators used in the prior art, it goes without saying that the measuring method of the present invention is not confined to such apparatus. The measuring apparatus of the present invention is not limited to those specific arrangements shown in the drawings. Various modifications and alterations can be made to the method and apparatus of the present invention within the scope of the appended claims.

We claim:

1. An apparatus for measuring physical quantities of a sheet object, comprising:
   a substantially cylindrical cavity electrode having a single means for both emitting and receiving microwave energy, said electrode including a cylindrical portion which is closed at one end and open at the other end, said opening being at a position facing said sheet object to be measured, and a substantially cylindrical protrusion at a substantially central portion of said electrode, said protrusion having a top or end surface facing an area of said sheet object to be measured, said top or end surface being substantially parallel to said sheet object so that electric fields become dense on the area of said sheet object to be measured; and
   a plate electrode larger than the opening of said substantially cylindrical electrode, and spaced apart from said opening to thereby provide a gap for insertion of said sheet object between said substantially cylindrical electrode and said plate electrode;
   said microwave emitting and receiving means emitting microwave energy into said substantially cylindrical electrode, and receiving microwave energy reflected by an inside wall of said substantially cylindrical electrode, said received microwave energy being attenuated and shifted in frequency at a resonance condition of said substantially cylindrical and plate electrodes when said sheet object is inserted within said gap.

2. The apparatus of claim 1, wherein said electrodes are made of plastics coated with metal.

3. The apparatus of claim 1, wherein said protrusion extends from said closed end of said substantially cylindrical electrode toward said open end thereof.

4. The apparatus of claim 3, wherein said protrusion terminates short of said open end of said substantially cylindrical electrode.

5. A system for measuring physical quantities comprising a plurality of fixed apparatus as set forth in claim 1 arranged in a metal block, and wherein said plate electrode is one integral plate covering said openings of said plurality of substantial cylindrical electrodes, for performing simultaneous measurement on a plurality of portions of said sheet object.

6. An apparatus for measuring physical quantities of a sheet object, comprising:
   a pair of substantially cylindrical cavity electrodes each having a single means for both emitting and receiving microwave energy, and each having openings at an end thereof, said substantially cylindrical electrodes being arranged opposed to each other with their respective openings facing each other, thereby providing a gap therebetween for insertion therein of said sheet object to be measured;
   a substantially cylindrical protrusion providing a substantially central portion of each of said substantially cylindrical electrodes as a part of the respective electrode, each said protrusion having top or end surfaces facing each other and facing an area of said sheet object to be measured, said top or end surfaces being substantially parallel to said sheet object so that electric fields become dense on said area to be measured; and
   said microwave emitting and receiving means emitting microwave energy into said electrodes, and receiving microwave energy reflected by an inside wall of said electrodes, said received microwaves being attenuated and shifted in frequency at a resonance condition of said electrodes when said sheet object is inserted within said gap.

7. The apparatus of claim 6, wherein the other end of each of said substantially cylindrical electrodes is closed, and said protrusions each extend from a respective closed end toward a corresponding respective open end.

8. The apparatus of claim 7, wherein said protrusions each terminate short of the respective open ends of their respective substantially cylindrical electrodes.

9. The apparatus of claim 7, wherein said electrodes are each made of plastics coated with metal.

10. The apparatus of claim 6, wherein said electrodes are each made of plastics coated with metal.

11. The apparatus of claim 6, wherein each of said protrusions has a penetrating hole therein.

12. The apparatus of claim 11, wherein said penetrating holes are substantially in the center of the respective protrusions, and extend completely through the respective substantially cylindrical electrode.

13. The apparatus of claim 11, wherein said electrodes are each made of plastics coated with metal.

14. An apparatus for measuring physical quantities of a stringy object, comprising:
   a substantially cylindrical microwave cavity resonator having a single means for both emitting and receiving microwave energy on a side wall thereof, and a substantially cylindrical protrusion provided on an axis thereof as part of said cavity resonator; and
   a penetrating cylindrical space for receiving therein said stringy object to be measured, said cylindrical space extending through said protrusion in an axial direction of said protrusion at a substantially central portion of said protrusion, said cylindrical space of said protrusion having an inside diameter which is small relative to a diameter of said cavity resonator so that a sufficient electric field penetrates into said stringy object received in said cylindrical space;
   said cavity resonator having a wall spaced from and facing an end of said penetrating cylindrical space of said protrusion;
   said microwave emitting and receiving means emitting microwave energy into said cavity resonator, and receiving microwave energy reflected by an inside wall of said cavity resonator, said received microwaves being attenuated and shifted in frequency at a resonance condition of said cavity resonator when said stringy object is received in said cylindrical space.

15. The apparatus of claim 14, further comprising a hole provided in said wall facing said penetrating cylindrical space of said protrusion, said hole being spaced from an end of said protrusion in the axial direction of said protrusion.

16. The apparatus of claim 15, wherein said cavity resonator is made of plastics material, and the inside surface thereof is coated with metal.

17. The apparatus of claim 14, wherein said cavity resonator is made of plastics material, and the inside surface thereof is coated with metal.

18. An apparatus for measuring physical quantities of a stringy object, comprising;
   a substantially cylindrical microwave cavity resonator having a single means for both emitting and receiving microwave energy on a side wall thereof, and a substantially cylindrical protrusion provided on an axis thereof as part of said cavity resonator; and
   a penetrating cylindrical space for receiving therein said stringy object to be measured, said cylindrical space extending through said protrusion in an axial direction of said protrusion at a substantially central portion of said protrusion, said cylindrical space of said protrusion having an inside diameter which is small relative to a diameter of said cavity resonator so that a sufficient electric field penetrates into said stringy object received in said cylindrical space;
   said cavity resonator having two of said protrusions arranged on a common axis, said two protrusions facing each other and being spaced apart from each other;
   said microwave emitting and receiving means emitting microwave energy into said cavity resonator, and receiving microwave energy reflected by an inside wall of said cavity resonator, said received microwaves being attenuated and shifted in frequency at a resonance condition of said cavity resonator when said stringy object is received in said cylindrical space.

19. The apparatus of claim 18, wherein said cavity resonator is made of plastics material, and the inside surface thereof is coated with metal.

20. A method of measuring moisture content x and basis weight y of a sheet object to be measured using a microwave cavity resonator, comprising:
   measuring frequency f and voltage v at the maximum resonance point of microwave energy on samples of a sheet object whose moisture content x and basis weight y are previously known;
   determining proportional constants of the following equations including at least product terms of x and y $$f = F_0 + F^1 \cdot x + F_2 \cdot y + F_3 \cdot xy + \ldots$$

$$v = V_0 + V^1 \cdot x + V_2 \cdot y + V_3 \cdot xy + \ldots$$

and then
   calculating moisture content x and basis weight y by the above equations using said determined values of proportional constants and measured values of frequency f and voltage v of the sheet object to be measured.

* * * * *

UNITED STATES PATENT AND TRADEMARK OFFICE
CERTIFICATE OF CORRECTION

PATENT NO. : 4,890,054

DATED : December 26, 1989

INVENTOR(S) : MAENO et al

It is certified that error appears in the above-identified patent and that said Letters Patent is hereby corrected as shown below:

Column 8, line 57, "providing" should read --provided at--.

Signed and Sealed this

Eighteenth Day of June, 1991

Attest:

HARRY F. MANBECK, JR.

Attesting Officer

Commissioner of Patents and Trademarks